United States Patent
Cermak

(10) Patent No.: US 7,926,776 B2
(45) Date of Patent: Apr. 19, 2011

(54) BRACKET FOR MOUNTING AT LEAST ONE POSITION DETECTING SENSOR ON AN ULTRASONIC PROBE

(75) Inventor: Craig J. Cermak, Riverside, IA (US)

(73) Assignee: CIVCO Medical Instruments Co., Inc., Kalona, IA (US)

( * ) Notice: Subject to any disclaimer, the term of this patent is extended or adjusted under 35 U.S.C. 154(b) by 403 days.

(21) Appl. No.: 12/111,387

(22) Filed: Apr. 29, 2008

(65) Prior Publication Data
US 2009/0266957 A1    Oct. 29, 2009

(51) Int. Cl.
*A47K 1/08* (2006.01)

(52) U.S. Cl. .............. 248/311.2; 248/309.1; 600/459; 601/2

(58) Field of Classification Search .......... 600/437–472; 601/2; 128/897; 248/346.03, 311.2, 309.1
See application file for complete search history.

(56) References Cited

U.S. PATENT DOCUMENTS

| | | | |
|---|---|---|---|
| 4,896,673 A | 1/1990 | Rose et al. | |
| 5,052,396 A | 10/1991 | Wedel et al. | |
| 5,076,269 A | 12/1991 | Austin | |
| 5,623,931 A | 4/1997 | Wung et al. | |
| 5,758,650 A | 6/1998 | Miller et al. | |
| 5,941,889 A | 8/1999 | Cermak | |
| 6,190,395 B1 | 2/2001 | Williams | |
| 6,332,891 B1 | 12/2001 | Himes | |
| 6,379,307 B1 | 4/2002 | Filly et al. | |
| 7,087,024 B1 | 8/2006 | Pruter | |
| 2004/0049111 A1 | 3/2004 | Hirooka et al. | |
| 2004/0230200 A1 | 11/2004 | Peterson | |
| 2005/0096536 A1 | 5/2005 | Peterson | |
| 2006/0072124 A1 | 4/2006 | Smetak et al. | |
| 2007/0167817 A1 | 7/2007 | Huang et al. | |
| 2008/0262356 A1 | 10/2008 | Chalana et al. | |
| 2009/0275833 A1* | 11/2009 | Ikeda et al. | 600/443 |
| 2010/0081920 A1* | 4/2010 | Whitmore et al. | 600/424 |

FOREIGN PATENT DOCUMENTS

| | | |
|---|---|---|
| EP | 1491158 A1 | 12/2004 |
| EP | 1932477 A1 | 6/2008 |
| EP | 1935365 A1 | 6/2008 |
| WO | 9610958 A2 | 4/1996 |

* cited by examiner

*Primary Examiner* — A. Joseph Wujciak, III
(74) *Attorney, Agent, or Firm* — Caesar, Rivise, Bernstein, Cohen & Pokotilow, Ltd.

(57) ABSTRACT

A bracket for use on an ultrasound transducer to releasably mount at least one 3D tracking sensor on the transducer. Each sensor has a pair of axially aligned pins projecting outward from its body. The bracket includes at least one socket having a pair of spaced-apart wall portions, each of which includes a slot arranged to receive a respective one of the pins of the sensor when the sensor is in a first position. From this position the sensor's body can be rotated to a second position, whereupon the spaced apart wall portions releasably engage (snap-fit about) a portion of the body of the sensor to deter the accidental displacement of the sensor with respect to the transducer.

16 Claims, 4 Drawing Sheets

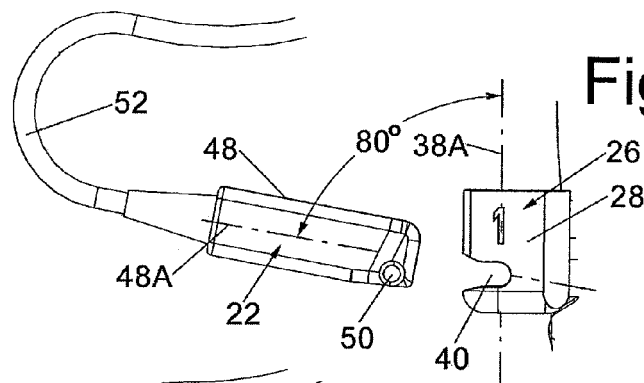
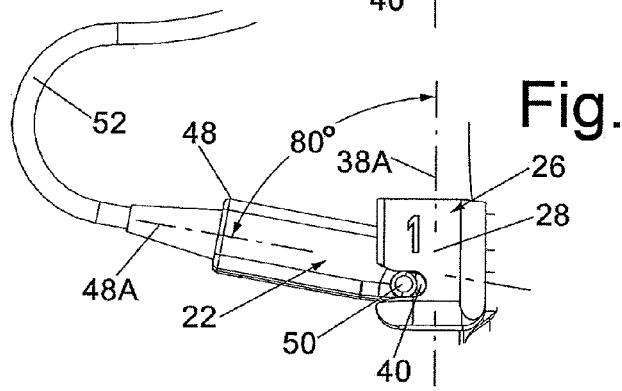
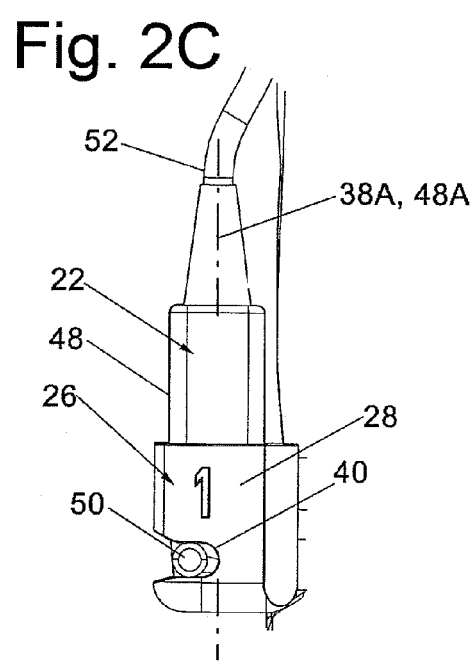
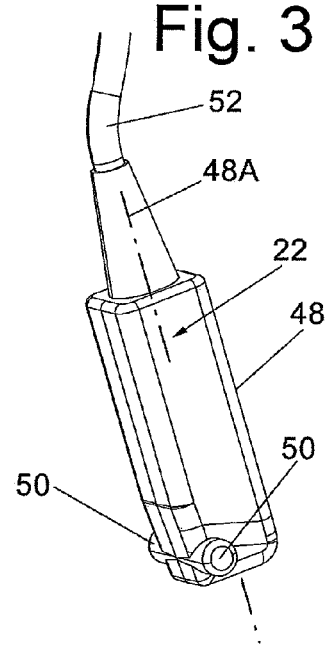

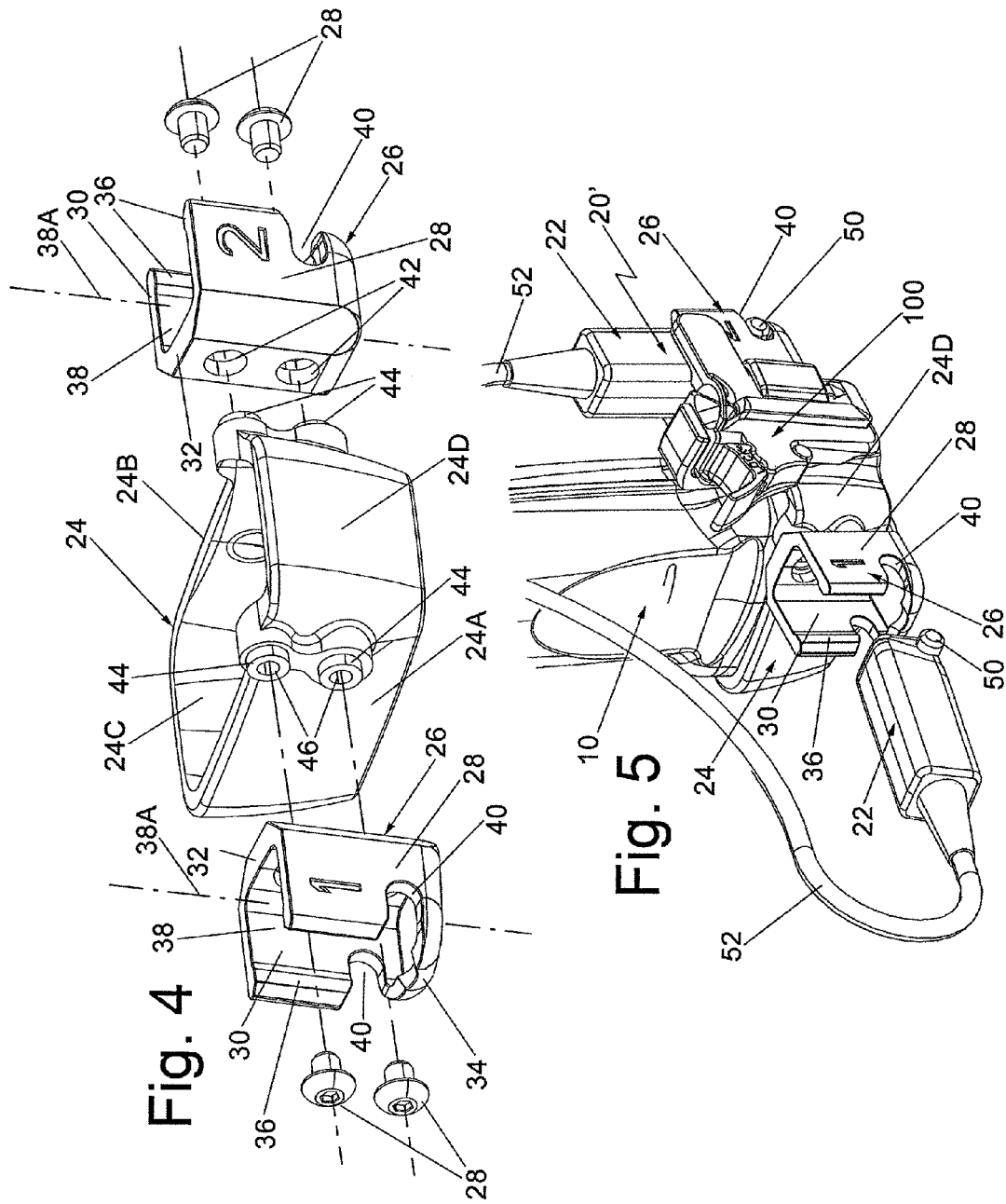

BRACKET FOR MOUNTING AT LEAST ONE POSITION DETECTING SENSOR ON AN ULTRASONIC PROBE

CROSS-REFERENCE TO RELATED APPLICATIONS

"Not Applicable"

STATEMENT REGARDING FEDERALLY SPONSORED RESEARCH OR DEVELOPMENT

"Not Applicable"

INCORPORATION-BY-REFERENCE OF MATERIAL SUBMITTED ON A COMPACT DISK

"Not Applicable"

FIELD OF THE INVENTION

This invention relates generally to medical devices and more particularly to devices for releasably mounting at least one sensor of a 3D tracking system on a ultrasound transducer or other hand-held medical instrument.

BACKGROUND OF THE INVENTION

Ultrasound has received widespread acceptance as a useful diagnostic tool by providing an image of the internal area of inquiry by emission of very high frequency sound waves from a transducer (commonly called a "probe") placed in contact with the patient's skin adjacent that area of inquiry. Repeated arrays of ultrasonic beams scan that area and are reflected back to the transducer, where the beams are received and the data transmitted to a processing device. A processing unit, to which the probe is connected, analyzes the information and composes a picture for display on an associated monitor screen. For some applications the determination of the precise position or location of the probe with respect to the patient's body is desirable, e.g., to correlate the ultrasonic image to other scans, such as CT scans.

So-called "3D tracking" systems are commercially available and disclosed in the patent literature for enabling one to readily determine the 3D position of an instrument, such as a medical device, by determining location, orientation, and/or positioning information relative to some coordinate system. For example, Ascension Technology Corporation makes 3D position and orientation tracking devices suitable for various medical applications, e.g., to navigating, localize, and guide medical instruments for image-guided procedures. Other manufacturers/suppliers of 3D tracking systems include Polhemus, Inc. Northern Digital Inc. and Medtronic, Inc.

Typically 3D tracking systems use the attenuation of oriented electromagnetic signals to determine the absolute position and orientation of a sensor, relative to a source, e.g., a DC magnetic field generator. The source and the sensor are connected via cables to an electronics module, which contains a microcomputer and associated electronics of the system. The source typically includes three orthogonal coils that are pulsed in rotation, one after another. Each pulse transmits a radio frequency electromagnetic signal that is detected by the sensor. The sensor also contains three orthogonal coils, which measure the strength of the signal from the current source coil. By using the known pulse strength at the source and the known attenuation of the strength with distance, the position and orientation of the sensor coils can be calculated by the system via triangulation techniques.

Utilizing device location or 3D tracking systems with ultrasonic probes can be accomplished by permanently mounting the sensor(s) on the probe or by building such sensor(s) into the probe. However, this approach may not be desirable if the probe is also intended to be used in applications wherein its position need not be determined, since the inclusion of such sensor(s) permanently on or in the probe will likely increase the cost and complexity of the probe. Moreover, such an approach may not be suitable to retrofit existing ultrasonic probes. Thus, the use of some releasable mounting system is deemed to be the better approach for providing an ultrasonic probe with means for determining its position with respect to the patient's body.

As will be appreciated by those skilled in the art, the prior art includes various brackets for releasable mounting devices on an ultrasonic probe. Such brackets are commonly used to support biopsy needle guides and the like. Examples of such brackets are disclosed in U.S. Pat. No. 5,052,396 (Wedel et al.), U.S. Pat. No. 5,076,269 (Arenson et al.), U.S. Pat. No. 5,623,931 (Wung et al.), U.S. Pat. No. 5,758,650 (Miller et al.), U.S. Pat. No. 5,941,889 (Cermak), U.S. Pat. No. 6,379,307 (Filly et al.), and U.S. Pat. No. 7,087,024 (Pruter). My prior U.S. Pat. No. 5,941,889 (Cermak) discloses and claims a multiple angle disposable needle guide system for use in guiding needles into selected locations of a patient relative to an ultrasonic probe or some other medical instrument imaging sensor.

While such brackets are suitable for their intended purposes, they are not designed for mounting one or more position sensors thereon. Accordingly, a need exists for such a bracket. Moreover, that bracket should be constructed so that the sensor(s) when mounted thereon will be resistant to accidental displacement, but can be readily removed and/or mounted when desired. This invention addresses those needs.

All references cited herein are incorporated herein by reference in their entireties.

SUMMARY OF THE INVENTION

In accordance with one aspect of this invention there is provided a bracket for use with an ultrasound transducer to releasably mount at least one sensor of a location/tracking system on the transducer. The at least one sensor has a body including an opposed pair of wall portions. The bracket comprises a member arranged to be releasably mounted on the transducer and includes at least one socket therein. The at least one socket has a pair of spaced-apart wall portions. The at least one socket and the at least one sensor are arranged to be coupled together via cooperating pins and slots to enable the at least one sensor to be oriented in a first position for insertion between the spaced-apart walls of the at least one socket to introduce said pins into respective ones of said slots so that the at least one sensor may be rotated to a second or locked position within the at least one socket. When the sensor is in the locked position, the wall portions of the at least one socket releasably engage, e.g., snap-fit, about a portion of the sensor to deter accidental displacement of the sensor with respect to the transducer.

In accordance with one exemplary embodiment of the bracket of this invention each of the wall portions of the at least one socket includes a slot and the pins project from the opposed wall portions of the at least one sensor and are axially aligned.

In accordance with another aspect of this invention there is provided the combination of a bracket and at least one sensor of a location/tracking system. The bracket and sensor are arranged for enabling the location of an ultrasound transducer to be determined. The sensor forms a part of a location/tracking system. The bracket comprises a member arranged to be releasably mounted on the transducer and includes at least one socket in it. The at least one socket has a pair of spaced-apart wall portions. The at least one socket and the at least one sensor are arranged to be coupled together via cooperating pins and slots to enable the at least one sensor to be oriented in a first position for insertion between the spaced-apart walls of the at least one socket to introduce said pins into respective ones of said slots so that the at least one sensor may be rotated to a second or locked position within the at least one socket. When the at least one sensor is in the locked position, the wall portions of the at least one socket releasably engage, e.g., snap-fit, about a portion of the at least one sensor to deter accidental displacement of the at least one sensor with respect to the transducer.

DESCRIPTION OF THE DRAWING

FIG. 2A is an side elevation view showing the sensor in an orientation wherein it is juxtaposed opposite a socket portion of a bracket like shown in FIG. 1 so that a sensor is ready for mounting therein;

FIG. 2B is an side elevation view, similar to FIG. 2A, showing the sensor at an initial position within the socket;

FIG. 2C is a side elevation view, similar to FIGS. 2A and 2B, but showing the sensor at its final or locked position within the socket, wherein it is resistant to accidental displacement;

FIG. 3 is an isometric view of the exemplary sensor shown in FIGS. 2A-2C;

FIG. 4 is an exploded isometric view of the various components making up the embodiment of the bracket shown in FIG. 1;

FIG. 5 is an isometric view of an alternative embodiment of a bracket constructed in accordance with this invention, the bracket of this embodiment including a fixed-angle biopsy needle guide assembly;

DETAILED DESCRIPTION OF THE PREFERRED EMBODIMENT

Figure 1:
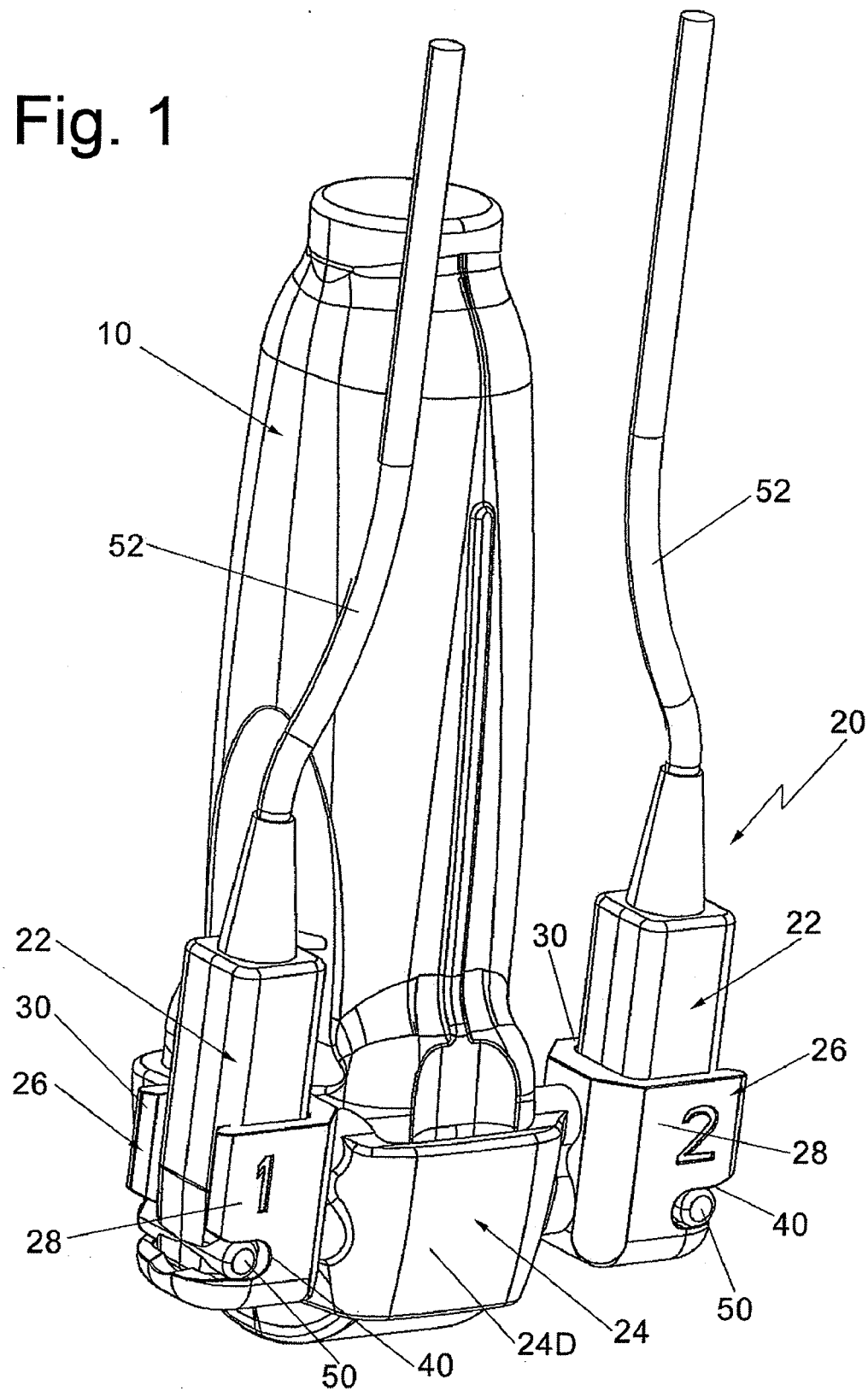
FIG. 1 is an isometric view of a portion of an ultrasonic probe having one exemplary embodiment of a bracket constructed in accordance with one aspect of this invention for supporting up to two position-locating sensors on the probe, so that those sensors are resistant to accidental displacement.

Referring now to the various figures of the drawing wherein like reference characters refer to like parts, there is shown in FIG. 1 a bracket 20 for use with an ultrasound transducer 10 to releasably mount one or more sensors 22 of a location sensing system, e.g., a 3D tracking system, such as available from Ascension Technology Corporation, or any other manufacturers of such systems. In the interest of drawing simplicity and brevity the other components of the locating sensing system are not shown. It should be pointed out at this juncture that subject invention can make use of any kinds of sensors for any kinds of 3D tracking systems whether based on electromagnetic, acoustic, mechanical, or optical technology. As such, the subject invention does not require any particular construction for the sensor, except that the body or housing of the sensor should be constructed to include a feature to be described shortly that ensures that when the sensor is in a locked position it is resistant to accidental displacement. In the exemplary embodiments shown and described herein such features comprise a pair of pins. However, other arrangements can be used as well.

The bracket 20 basically comprises a body portion 24 supporting one or more sockets 26. The details of the body portion 24 will be described later. Suffice for now to state that the body portion is arranged to be releasably mount the bracket 20 on the transducer 10. Each socket 26 is, in turn, arranged to releasably mount a respective one of the sensors 22 of the location sensing system. In the embodiment shown in FIG. 1, two such sensors 22 are shown mounted in respective sockets of the bracket 20 in their operative or locked position (i.e., a position wherein they are resistant to accidental displacement). It should be pointed out at this juncture that the bracket of the subject invention can be constructed to accommodate more than two sensors or only one sensor, depending upon the application.

The transducer 10 can be of any conventional or non-conventional construction and may be an ultrasonic transducer or any other hand-holdable probe or device for use with any type of scanning system where the position and orientation of the probe or device is desired to be determined. As best seen in FIGS. 1 and 4, the body portion 24 basically comprises a ring-like member which is arranged to snap-fit about a portion of the periphery of the probe 10, e.g., about the lower or distal portion of the probe as shown in FIG. 1. A sterilized cover (not shown) may be interposed between the probe and the bracket 20. In the exemplary embodiment shown, the ring-like body portion 24 is an integral member, e.g., a molded component formed of any suitable material, e.g., plastic, and includes four sidewall portions, namely, a left sidewall portion 24A, a right sidewall portion 24B, a front wall portion 24C and a rear wall portion 24D. In the exemplary embodiment of FIG. 1 two sockets 26 are mounted on the body portion 24. In particular, one socket 26 is mounted on the left sidewall portion 24A while the other socket 26 is mounted on the right sidewall portion 24A. The mounting of the sockets on their respective sidewalls is accomplished by use of respective pairs of threaded fastener 28 as shown clearly in FIG. 4. These fasteners are arranged to extend through respective holes (to be described later) in the sockets for receipt in respective holes (also to be described later) in bosses (also to be described later) formed on the respective sidewalls of the ring-like body member 24.

The details of the sockets 26 will now be described with reference to FIG. 4. As can be seen therein each socket 26 is a generally U-shaped member, e.g., an integral molded component formed of any suitable material, e.g., plastic. Each socket 26 basically comprises a member having a pair of opposed sidewalls 28 and 30, a back wall 32 that bridges the sidewalls 28 and 30 along their full length and a front wall 34 that bridges the bottom ends of the sidewalls 28 and 30. The free end of each of the sidewalls 28 and 30 is in the form of a slight cam surface lip or flange 36. The contiguous walls 28, 30, 32 and 34 define an internal cavity 38 which is arranged for receipt of the body of the sensor 26. The cavity 38 has a longitudinal (e.g., vertical in FIG. 4) axis 38A. The entrance to the cavity 38 is the gap between the cam surface flanges 36 of the sidewalls 28 and 30. The gap extends generally parallel to the longitudinal axis 38A of the socket's cavity. It is through this gap that the sensor is introduced into the cavity 38.

Each of the sidewalls 28 and 30 includes a horizontally oriented slot 40. Each slot 40 is located immediately above the front wall 34 where the front wall meets the sidewall in which the slot is located. The innermost end of each slot 40 is semicircular in shape and of a predetermined radius to accommodate a respective pin (to be described later) of the sensor 22. The back wall 32 of each socket 26 includes a pair of openings 42 through which the heretofore mentioned fasteners 28 extend for mounting the socket on the ring-like body member 24. As mentioned earlier the ring-like body member includes a pair of bosses and associated holes to receive the fasteners. In particular a pair of bosses 44 projects outward from the outer surface of the sidewall portion 24A of the body portion 24, while a similar pair of bosses 44 projects outward from the outer surface of the sidewall portion 24B. A hole 46 extends through each of the bosses 44. It is in the hole 46 that a portion of and associated fastener 28 resides to secure the socket 26 to the ring-like body member 24.

The details of the sensors 22 will now be described with reference to FIGS. 1 and 3. To that end, each sensor 22 basically comprises an elongated body 48 having a longitudinal axis 48A. The sensor's body may be formed of any suitable material, e.g., a molded plastic, and houses the components (not shown) making up the sensor.

As mentioned earlier, each sensor includes a pair of pins for cooperation with the sockets to render the sensor resistant to accidental displacement from that socket when the sensor is in the locked position. Those pins are designated by the reference number 50 and are best seen in FIG. 3. The pins 50 are axially aligned pins project outward from a lower portion of sensor's body 48 perpendicularly to its longitudinal axis 48A. A cable 52 projects outward from the upper end of the sensor for connection to the associated component of the 3D tracking system. In the exemplary embodiments shown herein the sensor's body is of a generally parallelepiped shape. However, other elongated shapes, e.g., cylindrical, oval, hexagonal, etc., can clearly be utilized for the sensor. Each of the axially aligned pins has an outside diameter just slightly less than the width of the slots 40 in the sidewalls 28 and 30 of the sockets 26 so that the pins 50 can be inserted therein for ultimate residence at the semi-circular inner end of the slot 40. In order to facilitate the entry of the pins into the slots the entry to each of the slots 40 is flared or chamfered slightly as best seen in FIGS. 2A-2C.

The manner of mounting each sensor into its respective socket will now be described with reference to FIGS. 2A-2C. To that end, the sensor 22 is oriented at a first position so that its lower end is juxtaposed opposite the socket 26 an wherein its longitudinal axis 48A is at an angle of approximately 80 degrees to the longitudinal axis 38A of the socket's cavity as shown in FIG. 2A. The probe is then moved towards the socket so that its pins 50 enter into the respective slots 40 in the sidewalls 28 and 30 as shown in FIG. 2B until the pins reach the semi-circular ends of those slots. The sensor is then rotated upward, i.e., towards the longitudinal axis 38A of the socket using the pins 50 as the pivot axis. This action causes the body 48 of the sensor to enter into the gap between the cam ends 36 of the sidewalls 28 and 30, whereupon those sidewalls flex apart slightly to allow the body 48 of the sensor to pass therebetween. When the longitudinal axis 48A of the sensor's body 48 is in a second position that is parallel to the longitudinal axis 38A of the socket, the body portion of the sensor will be fully within the socket, whereupon the sidewalls 28 and 30 snap back into place thereby locking the sensor in the cavity of the socket. This second position is the heretofore mentioned locked position, wherein the sensor is resistant to accidental displacement with respect to the bracket. In particular, the cam flanges on the ends of the sidewalls 28 and 30 will prevent lateral displacement of the probe, while the residence of the pins 50 within the slots 40 will prevent longitudinal displacement, e.g., displacement which could occur if the sensor's cable is accidentally pulled.

Notwithstanding the above, dismounting of any sensor can be readily accomplished when desired by merely pivoting the sensor 22 in the counter-clockwise direction, i.e., away from the longitudinal axis 38A of the socket, from its locked position shown in FIG. 2C, whereupon the body 48 of the sensor passes through the gap between the cam surfaces 36 on the ends of the sidewalls 28 and 30. Continued rotation of the sensor 22 in that rotational direction with respect to the socket 26 will bring it to the orientation wherein its longitudinal axis 48A is at an angle of approximately 80 degrees to the longitudinal axis 38A of the socket. When the sensor is in this orientation (such as shown in FIG. 2B), the sensor can be pulled laterally away from the socket, like shown in FIG. 2A, thereby dismounting it from the bracket. It should be pointed out that the acute angle of 80 degrees at which the sensor body is oriented to introduce its pins 50 into the slots 40 to either mount the sensor or dismount the sensor is merely exemplary. Thus, the bracket of the subject invention can be constructed so that the entry angle of the sensor is at whatever angle is desired, e.g., perpendicular or at some acute angle less than 90 degrees.

Each sensor 22 may be mounted in or dismounted from each socket 26 in the same manner as described above. Moreover, while the embodiment of the bracket 20 shown in FIG. 1 includes two sockets, each identified with respective indicia, i.e., the number "1" embossed on the sidewall 28 of one socket and the number "2" embossed on the sidewall 28 of the other socket, to permit up to two sensors to be used at one time, that is not obligatory. Thus, only one sensor may be mounted on the bracket at any one time for some procedure and that sensor may be mounted within either socket #1 or socket #2.

In FIG. 5 there is shown a second embodiment of a bracket 20' constructed in accordance with this invention. The bracket 20' is identical in construction to bracket 20 except that it includes a conventional biopsy needle guide assembly 100 mounted on the rear wall 24D. The needle guide can be of any desired construction. In this embodiment the needle guide is a fixed angle needle guide, i.e., a guide wherein the angle that the biopsy needle is introduced into the patient's body via the transducer is a fixed, predetermined angle.

Figure 6:
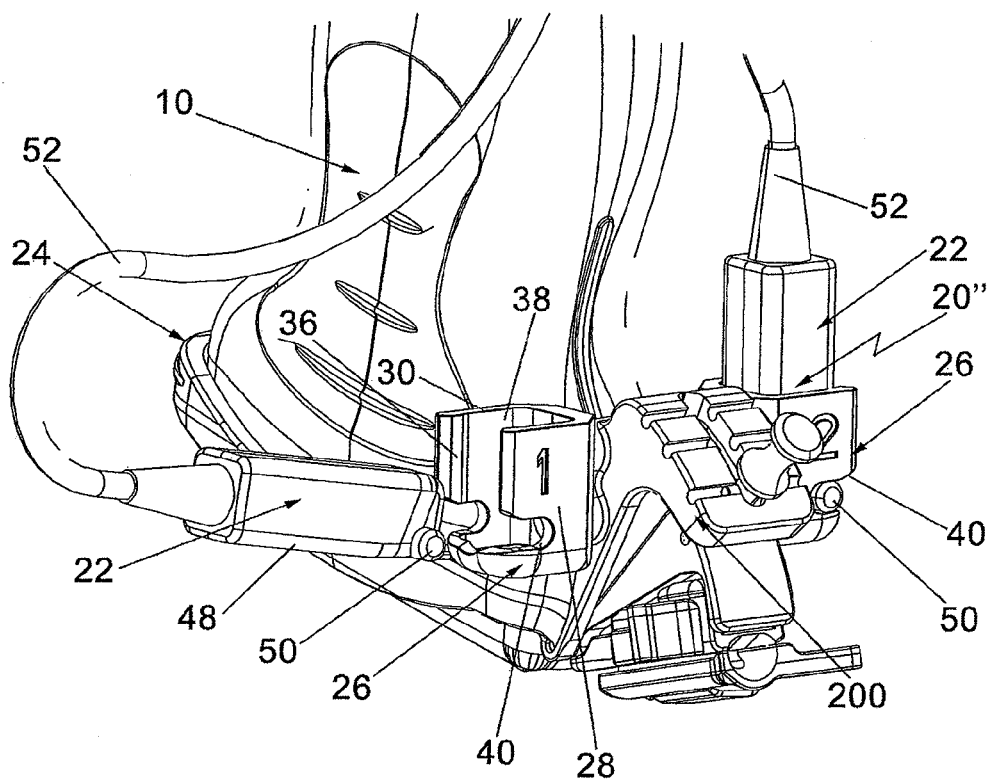
FIG. 6 is an isometric view similar to FIG. 5, but showing still another embodiment of a bracket constructed in accordance with this invention, the bracket of this embodiment including an adjustable angle biopsy needle guide assembly.

In FIG. 6 there is shown a third embodiment of a bracket 20" constructed in accordance with this invention. The bracket 20" is identical in construction to bracket 20' except that it includes an adjustable angle biopsy needle guide assembly 200 mounted on the rear wall 24D. The adjustable needle guide assembly 200 is preferably constructed in accordance with the teachings of my aforementioned U.S. Pat. No. 5,941,889, which as mentioned above is incorporated by reference herein, so that the biopsy needle can be introduced into the patient's body from any one of several predetermined angles. Other adjustable needle guides can be used in lieu of that adjustable needle guide.

It should be pointed out at this juncture, that while the exemplary preferred embodiments disclosed above make use of the projecting pins being located on the sensor, it is contemplated that the pins form a portion of the sockets, e.g., extend inward into the cavity 38 from respective sidewalls 28 and 30, in which case the body 48 of the sensor would have to include appropriately configured slots or recesses to enable the pins of the socket to be received therein so that the sensor can be pivoted from an initial position to a locked position and vice versa.

Without further elaboration the foregoing will so fully illustrate my invention that others may, by applying current or future knowledge, adopt the same for use under various conditions of service.

I claim:

1. A bracket for use with an ultrasound transducer to releasably mount at least one sensor of a location sensing system on the transducer, said at least one sensor having a body including an opposed pair of wall portions, said bracket comprising a member arranged to be releasably mounted on the transducer and including at least one socket therein, said at least one socket having a pair of spaced-apart wall portions, said at least one socket and said at least one sensor being arranged to be coupled together via cooperating pins and slots to enable said at least one sensor to be oriented in a first position for insertion between said spaced-apart walls of said at least one socket to introduce said pins into respective ones of said slots so that said at least one sensor may be rotated to a second position within said at least one socket, whereupon said wall portions releasably engage a portion of said at least one sensor to deter accidental displacement of said at least one sensor with respect to the transducer.

2. The bracket of claim 1 wherein said at least one sensor comprises said pins, said pins projecting from said opposed wall portions of said at least on one sensor and are being axially aligned, and wherein each of said wall portions of said at least one socket includes a slot, said slots of said at least one socket being arranged for receipt of respective ones of said pins of said at least one sensor.

3. The bracket of claim 2 wherein said at least one sensor comprises an elongated body having a longitudinal axis, and wherein said axially aligned pins project outward from a lower portion of said body perpendicular to said longitudinal axis and wherein said slots of said at least one socket are axially aligned for receipt of said axially aligned pins.

4. The bracket of claim 3 wherein said at least one socket includes a longitudinal axis and wherein the longitudinal axis of said at least one sensor is oriented parallel to said longitudinal axis of said at least one socket when said at least one sensor is in the second position.

5. The bracket of claim 4 wherein the longitudinal axis of said at least one sensor is oriented at an acute angle to said longitudinal axis of said at least one socket when said at least one sensor is in said first position.

6. The bracket of claim 1 wherein said wall portions snap fit about portions of said at least one sensor.

7. The bracket of claim 4 wherein said wall portions snap fit about portions of said at least one sensor.

8. The bracket of claim 1 wherein said bracket includes a ring-like member for encircling a portion of the transducer to releasably mount said bracket thereon.

9. In combination a bracket for use with an ultrasound transducer to releasably mount at least one sensor of a location sensing system on the transducer, said at least one sensor having a body including an opposed pair of wall portions, said bracket comprising a member arranged to be releasably mounted on the transducer and including at least one socket therein, said at least one socket having a pair of spaced-apart wall portions, said at least one socket and said at least one sensor being arranged to be coupled together via cooperating pins and slots to enable said at least one sensor to be oriented in a first position for insertion between said spaced-apart walls of said at least one socket to introduce said pins into respective ones of said slots so that said at least one sensor may be rotated to a second position within said at least one socket, whereupon said wall portions releasably engage a portion of said at least one sensor to deter accidental displacement of said at least one sensor with respect to the transducer.

10. The combination of claim 9 wherein said pins project from said opposed wall portions of said at least one sensor and are axially aligned, and wherein each of said wall portions of said at least one socket includes a slot, said slots of said at least one socket being arranged for receipt of respective ones of said pins of said at least one sensor.

11. The combination of claim 10 wherein said sensor comprises an elongated body having a longitudinal axis and wherein said axially aligned pins project outward from a lower portion of said body perpendicular to said longitudinal axis.

12. The combination of claim 11 wherein said at least one socket includes a longitudinal axis and wherein said longitudinal axis of said at least one sensor is oriented parallel to said longitudinal axis of said at least one socket when said at least one sensor is in said second position.

13. The combination of claim 12 wherein the longitudinal axis of said at least one sensor is oriented at an acute angle to said longitudinal axis of said at least one socket when said at least one sensor is in said first position.

14. The combination of claim 9 wherein said wall portions snap fit about portions of said at least one sensor.

15. The combination of claim 10 wherein said wall portions snap fit about portions of said at least one sensor.

16. The combination of claim 9 wherein said bracket includes a ring-like member for encircling a portion of the transducer to releasably mount said bracket thereon.

* * * * *